United States Patent [19]  [11] 4,216,152
Schneider et al.  [45] Aug. 5, 1980

[54] PROCESS FOR MAKING N-(N'-METHYLENEPYRROLIDONYL)-2-SUBSTITUTED ANILINES

[75] Inventors: Louis Schneider, Elizabeth; David E. Graham, Westfield, both of N.J.

[73] Assignee: GAF Corporation, New York, N.Y.

[21] Appl. No.: 969,360

[22] Filed: Dec. 14, 1978

Related U.S. Application Data

[63] Continuation-in-part of Ser. No. 892,146, Mar. 31, 1978, and Ser. No. 955,483, Oct. 27, 1978.

[51] Int. Cl.$^2$ ............... A01N 9/22; C07D 207/26
[52] U.S. Cl. ............... 260/326.5 S; 71/95; 260/326.5 FL; 568/584
[58] Field of Search ............... 260/326.5 FL

[56] References Cited

U.S. PATENT DOCUMENTS

| | | | |
|---|---|---|---|
| 3,651,085 | 3/1972 | Lunsford | 260/326.5 J |
| 3,769,301 | 10/1973 | Olin | 260/326.45 |

OTHER PUBLICATIONS

Morrison, R. and R. Boyd, "Organic Chemistry", 3rd ed., Allyn and Bacon, Inc., Boston, (1974), p. 742.

*Primary Examiner*—Donald G. Daus
*Assistant Examiner*—Lisa Jones
*Attorney, Agent, or Firm*—Walter C. Kehm; Walter Katz

[57] ABSTRACT

This invention relates to an improved process for making N-(N'-methylenepyrrolidonyl)-2-substituted anilines which are useful intermediates in the synthesis of agricultural herbicides.

This process of the invention comprises reacting a 2-substituted aniline with N-chloromethylpyrrolidone at about room temperature in the presence of an acid acceptor. Such room temperature alkylation of the aniline prevents excessive side reactions, particularly with a substituent in the 2-position of the aniline, such as an alkenyl group, which is sensitive to alkylating agents which require excessive heating to effective the condensation reaction.

3 Claims, No Drawings

PROCESS FOR MAKING N-(N'-METHYLENEPYRROLIDONYL)-2-SUBSTITUTED ANILINES

This application is a continuation-in-part of Ser. Nos. 892,146, filed Mar. 31, 1978; and 955,483, filed on Oct. 27, 1978.

BACKGROUND OF THE INVENTION

1. Field of the Invention

This invention relates to a process of making N-(N'-methylenepyrrolidonyl)-2-substituted anilines which are intermediates in making useful herbicides.

2. Description of the Prior Art

U.S. Pat. Nos. 3,769,301 and 3,907,544 disclose related herbicidal compounds; however, these compounds are made by a different process. Accordingly, it is an object of this invention to provide a new and improved process for making intermediates in the synthesis of herbicidally active compounds.

U.S. Pat. Nos. 3,853,910 and 3,956,313 describes a condensation reaction of N-methylolpyrrolidone with alcohols and thioalcohols, respectively, in the presence of an acid catalyst. U.S. Pat. No. 4,105,671 discloses a similar reaction at elevated temperatures.

SUMMARY OF THE INVENTION

This invention relates to a process for making N-(N'-methylenepyrrolidonyl)-2-substituted aniline intermediate compounds in high yield having the formula:

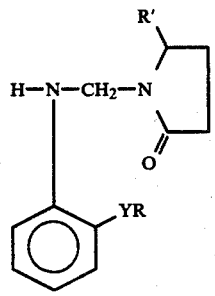

where R is
  alkyl, $C_1$–$C_6$,
  alkenyl, $C_3$–$C_5$,
  alkyleneoxyalkyl, —$(CH_2)_n OR''$, where n=1–3, and R'' is alkyl, $C_1$–$C_3$, or cycloalkyl,

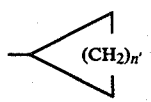

where n'=0–3,
R' is hydrogen or alkyl, $C_1$–$C_3$, and
Y is oxygen or sulfur.

The process comprises reacting a mixture containing substantially equivalent molar amounts of a chloromethylpyrrolidone having the formula:

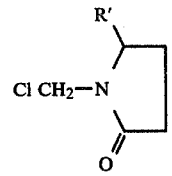

and a 2-substituted aniline, having the formula:

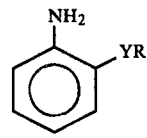

Where R, R' and Y are as defined above, in a solvent, in the presence of an acid acceptor, at about room temperature, and crystallizing the product from the resulting solution.

Since the process is carried out at room temperature, substituents which are sensitive to excessive heating required of other alkylating agents, form the desired product in high yield without undesirable side reactions. For example, an alkenyl substituent is considered a group for the best mode of the invention.

DETAILED DESCRIPTION OF THE INVENTION

The starting material in the process of this invention is a 2-substituted aniline which is usually commercially available; otherwise it is made from 2-nitrophenol or 2-nitrothiophenol by reaction with a halogenated alkyl ether, a cycloalkyl halide, an alkyl halide or an alkenyl halide, to form the 2-substituted oxynitrobenzene or 2-substituted thionitrobenzene. The nitro group then is reduced to the corresponding aniline. N-chloromethylpyrrolidone is obtained from N-methylolpyrrolidone by halogenation with thionyl chloride, as described in Chemical Abstracts 54, 1286f (1960).

The essential step in the overall process, which is the subject of this invention, is the reaction of the thus-prepared 2-substituted aniline with N-chloromethylpyrrolidone to form the desired N-(N'-methylenepyrrolidonyl)-2-substituted aniline. As the feature of the invention, this condensation is carried out at about room temperature, thus preventing side reactions from occurring with substituents which are sensitive to the high reaction temperatures required with other alkylating agents, such as N-methylolpyrrolidone. For groups such as alkenyl, for example, room temperature alkylation is advantageous in providing the desired product in high quality and in high yield.

The intermediate compounds produced by the process of the invention are acylated with a haloacetyl halide to form the corresponding N-(haloacetyl) derivatives, which are useful herbicides.

As used herein, the term "alkyl" includes both straight and branched chain hydrocarbon radicals; the term "alkenyl" includes straight, branched chain and cyclic hydrocarbons.

PREPARATION OF N-CHLOROMETHYLENEPYRROLIDONE

N-Methylolpyrrolidone (225 g., 1.95 mole) and toluene (400 cc) were chilled to 5° C. with stirring and thionyl chloride (257 ml., 3.3 mole) in toluene (300 cc) was added dropwise in 2 hrs. The mixture was allowed to remain overnight. The toluene solvent then was rotoevaporated and the residue distilled at 107°–110° C. at 2.5–3 mm. Hg yielding 151.5 g (58.2%) of product which crystallized on standing, m.p. 35°–37° C.

The Examples which follow will more particularly illustrate the invention without being limiting thereof.

EXAMPLE 1

N-(N'-Methylenepyrroliodonyl)-2-Propoxyaniline o-Propoxyaniline (10 g., 0.07 mole), sodium carbonate (7.0 g.) and toluene (60 ml) were chilled to 5° C. with stirring and N-chloromethylenepyrrolidone (8.8 g., 0.07 mole) in toluene (40 cc) was added dropwise during ½ hr. The mixture was allowed to stand overnight at room temperature. Then 100 ml water was added, the toluene layer was removed, and the residue was rotoevaporated to give 14.4 g. of crude product which was recrystallized from methanol yielding 9.0 g. of product (54.8%), m.p. 83°–84° C.

EXAMPLE 2

N-(N'-Methylene-2-Pyrrolidonyl)-2-Cyclopentoxyaniline

A. 2-Cyclopentoxynitrobenzene

2-Nitrophenol (83.5 g, 0.60 mole), cyclopentyl bromide (98.0 g, 0.66 mole), anhydrous potassium carbonate (82.9 g, 0.60 mole) and dry acetone (600 cc) were refluxed for 72 hours, and filtered to remove the potassium bromide. The residue was washed with acetone and the solvent was removed by rotary evaporation. The residue was partitioned between 200 cc of dichloromethane and water. The dichloromethane layer was washed with 200 cc of 10% potassium hydroxide, separated and the solvent was removed by rotary evaporation. The crude product was fractionally distilled at 144°–146° C. at 1.0 mm. Hg to yield 58.2 g of product (46.8%).

B. 2-Cyclopentoxyaniline

Iron 60 mesh (51.9 g, 0.93 mole), water (220 cc), ethanol (244 cc) and concentrated hydrochloric acid (14.2 cc) were heated to reflux under a nitrogen blanket. Then 2-cyclopentoxynitrobenzene (55.2 g, 0.27 mole) was added at reflux over a period of 2 hours. The reaction was maintained at reflux for an additional 3 hours. The pH was adjusted to 7–8 by the addition of concentrated ammonium hydroxide. The reaction mixture then was filtered at 30° C., and the filtrate was washed with 200 cc of ether. The filtrate was extracted with 4×50 cc of ether and the combined ether extracts were subjected to rotary evaporation. The crude product was fractionally distilled at 126°–130° C. at 2.0–2.5 mm. Hg to yield 30.3 g (64.3%) of product.

C. 2-cyclopentoxyaniline,

N-chloromethyl-2-pyrrolidone, sodium carbonate and xylene then were reacted as in Example 1, and the reaction mixture was worked up to provide the desired product, m.p. 87°–87.5° C.

EXAMPLE 3

N-(5-Methyl-N'-Methylene-2-Pyrrolidonyl)-2-Methylmercaptoaniline

2-Methylmercaptoaniline, 5-methyl-N-chloromethyl-2-pyrrolidone, sodium carbonate and toluene were reacted in a similar manner as described in Example 1 to produce the desired product.

EXAMPLE 4

N-(N'-Methylene-2-Pyrrolidonyl)-2-Butylmercaptoaniline

2-Butylmercaptoaniline was prepared from -2-nitrothiophenol by a two-step reaction sequence consisting of alkylation followed by reduction. The aniline then was condensed with N-chloromethyl-2-pyrrolidone to yield the desired product.

EXAMPLE 5

N-(N'-Methylene-2-Pyrrolidonyl)-2-Propen-2-yl-mercaptoaniline

2-Propen-2-yl-mercaptoaniline was prepared by reduction of 2-propen-2-yl-mercaptonitrobenzene, which was obtained by condensing 2-nitrothiophenol and allyl bromide, to give the corresponding aniline.

Then 2-propen-2-yl-mercaptoaniline, N-chloromethyl-2-pyrrolidone and sodium carbonate were condensed in toluene to form the desired product.

EXAMPLE 6

N-(N'-Methylene-2-Pyrrolidonyl)-2-Ethoxyethylmercaptoaniline

2-Ethoxyethylmercaptoaniline was prepared by reduction of 2-ethoxyethylmercaptonitrobenzene, which was obtained by condensation of 2-nitrothiophenol and 2-bromoethyl ethyl ether, to give the corresponding aniline. The 2-ethoxyethylmercaptoaniline and N-chloromethyl-2-pyrrolidone were then condensed in toluene to form the product in high yield.

EXAMPLE 7

N-(N'-Methylene-2-Pyrrolidonyl)-2-Cyclopentylmercaptoaniline

2-Cyclopentylmercaptoaniline was prepared by reduction of 2-cyclopentylmercaptonitrobenzene, which was obtained from 2-nitrothiophenol and bromocyclopentane followed by reduction to the corresponding aniline. The 2-cyclopentylmercaptoaniline was subsequently condensed with N-chloromethylenepyrrolidone in toluene in the presence of sodium carbonate to form the desired product.

EXAMPLE 8

N-(N'-Methylene-2-Pyrrolidonyl)-2-Ethoxyethoxyaniline

A. 2-Ethoxyethoxynitrobenzene

2-Nitrophenol (91.0 g., 0.65 mole), 2-bromoethyl ethyl ether (100.0 g., 0.65 mole), anhydrous potassium carbonate (9.0 g, 0.72 mole) and acetone (1 liter) were refluxed for 65 hours. The reaction mixture was filtered, and the acetone removed by rotary evaporation. The residue was partitioned between 200 ml. of dichloromethane and 100 ml. water. The organic phase was further washed with 200 ml. of 10% sodium hydroxide followed by 100 cc of water. The product (58.0 g) was obtained in 42% yield by a vacuum distillation (100°–120° C./0.5 mm).

B. 2-Ethoxyethoxyaniline

Iron 60 mesh (54.0 g, 0.96 mole), concentrated hydrochloric acid (15 cc), ethanol (260 cc) and water (230 cc)

were heated to reflux under a nitrogen blanket; 2-ethoxyethoxynitrobenzene (58.0 g, 0.28 mole) was added at reflux over 4 hours, and reflux continued for an additional 3 hours. The reaction mixture then was neutralized with concentrated ammonium hydroxide to a pH of 8–9, and filtered through a Celite bed. The iron cake was washed with 200 cc of ether, and the organic phase was separated. The product (20.0 g) was obtained in 40.2% yield by a vacuum distillation (111°–135° C./2–4 mm).

C. 2-Ethoxyethoxyaniline,

N-chloromethyl-2-pyrrolidone, sodium carbonate and xylene were reacted as in Example 1 to form the desired product.

EXAMPLE 9

N-(N'-Methylene-2-Pyrrolidonyl)-2-Prop-1-en-oxyaniline

A. 2-Prop-1-en-oxynitrobenzene

2-Nitrophenol (142.0 g, 1.02 mole), allyl bromide (120.9 g, 1.00 mole), anhydrous potassium carbonate (140.0 g, 1.02 mole) and dry acetone (500 cc) were refluxed for 21 hours, and filtered to remove the potassium bromide. The residue was washed with acetone and the solvent was removed by rotary evaporation. The residue was partitioned between 200 cc of dichloromethane and water. The dichloromethane layer was washed with 200 cc of 10% potassium hydroxide, separated and the solvent was removed by rotary evaporation. The crude product was fractionally distilled at 124° C. at 2.0 mm. Hg to yield 164.7 g of product (91.9%).

B. 2-Prop-1-en-oxyaniline

Iron 60 mesh (106.3 g, 1.9 mole), water (450 cc), ethanol (500 cc) and concentrated hydrochloric acid (29.5 cc) were heated to reflux under a nitrogen blanket. Then 2-prop-1-en-oxynitrobenzene (89.6 g, 0.57 mole) was added at reflux over a period of 2 hours. The reaction was maintained at reflux over a period of 2 hours. The reaction was maintained at reflux for an additional 3 hours. The pH was adjusted to 7–8 by the addition of concentrated ammonium hydroxide. The reaction mixture then was filtered at 30° C., and the filtrate was washed with 200 cc of ether. The filtrate was extracted with 4×50 cc of ether and the combined ether extracts were subjected to rotary evaporation. The crude product was fractionally distilled at 110°–112° C. at 4.5 mm Hg to yield 50.1 g. (67.2%) of product.

C.

2-Prop-1-en-oxyaniline (5.6 g., 0.037 mole), sodium carbonate (3.9 g., 0.037 mole) and toluene (50 ml) were chilled to 5° C. with stirring and N-chloromethylpyrrolidone (5.0 g., 0.037 mole) in toluene (20 cc) was added dropwise during ¼ hr. and allowed to stand overnight. Then 100 ml water was added to the mixture; the toluene layer was filtered, and rotoevaporated to give a crude product which was recrystallized from ether yielding 6.8 of product (75.0%), m.p. 79°–81° C.

EXAMPLE 10

N-(N'-Methylene-2-Pyrrolidonyl)-2-But-1-en-oxyaniline

4-Bromobutene-1 was reacted with o-nitrophenol to yield 2-but-1-en-oxynitrobenzene; which was reduced to the corresponding aniline; and reacted with N-chloromethyl-2-pyrrolidone to form the corresponding N-methylenepyrrolidonyl derivative.

EXAMPLE 11

N-(N'-Methylene-2-Pyrrolidonyl)-2-(2-Methylprop-1-en-oxy)aniline

3-Chloro-2-methyl propene was reacted with o-nitrophenol to yield 2-(2-methylprop-1-en-oxy) nitrobenzene; which was reduced to the corresponding aniline; and reacted with N-chloromethyl-2-pyrrolidone to form the corresponding N-methylenepyrrolidonyl derivative.

EXAMPLE 12

N-(N'-Methylene-2-Pyrrolidonyl)-2-But-2-en-oxyaniline

2-Bromo-but-2-ene was reacted with o-nitrophenol to yield 2-but-1-en-oxynitrobenzene; which was reduced to the corresponding aniline; then reacted with N-chloromethyl-2-pyrrolidone to form the corresponding N-methylene-2-pyrrolidonyl derivative.

EXAMPLE 13

N-(5-Methyl-N'-Methylene-2-pyrrolidonyl)-2-Prop-1-en-oxyaniline

Allyl bromide was reacted with o-nitrophenol to yield 2-prop-1-en-oxynitrobenzene; which was reduced to the corresponding aniline; then reacted with 5-methyl-N-chloromethyl-2-pyrrolidone to form the corresponding 5-methyl-N'-methylene-2-pyrrolidonyl derivative.

EXAMPLE 14

N-(5-methyl-N'-Methylene-2-pyrrolidonyl)-2-Cyclopent-3-en-oxyaniline

Cyclo-pent-3-en-1-ol was reacted with o-nitrophenol to yield 2-cyclopent-3-en-oxynitrobenzyene; which was reduced to the corresponding aniline; then reacted with 5-methyl-N-chloromethyl-2-pyrrolidone to form the corresponding 5-methyl-N'-methylene-2-pyrrolidonyl derivative.

What we claim is:

1. A process for making N-(N'-methylenepyrrolidonyl)-2-substituted aniline intermediate compounds in high yield having the formula:

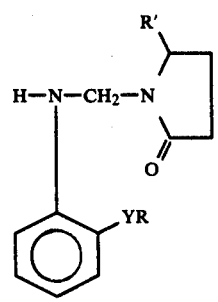

where R is
alkyl, $C_1$–$C_6$,
alkenyl, $C_3$–$C_5$,
alkyleneoxyalkyl, —$(CH_2)_nOR''$, where n=1–3, and R'' is alkyl, $C_1$–$C_3$, or cycloalkyl,

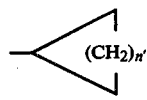

where n'=0–3,
R' is hydrogen or alkyl, $C_1$–$C_3$, and,
Y is oxygen or sulfur,
which consists of:
(a) forming a mixture containing substantially equivalent molar amounts of a chloromethylpyrrolidone having the formula:

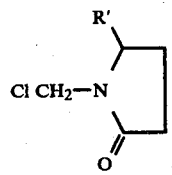

and a 2-substituted aniline having the formula:

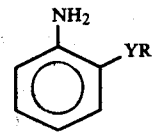

by adding said chloromethylpyrrolidone to said 2-substituted aniline at a temperature of about 5° C. or less, at atmospheric pressure, in an aromatic hydrocarbon solvent, in the presence of an acid acceptor, and
(b) warming said mixture to about room temperature
(c) reacting said reactants until alkylation is substantially complete, and,
(d) crystallizing the product from the resulting solution.

2. A process according to claim 1 wherein R is alkenyl.

3. A process according to claim 1 wherein said solvent is toluene or xylene.